United States Patent
Ugarov (10) Patent No.: US 9,607,817 B1
(45) Date of Patent: Mar. 28, 2017

(54) SYSTEMS AND METHODS FOR ION SEPARATION

(71) Applicant: Thermo Finnigan LLC, San Jose, CA (US)

(72) Inventor: Mikhail V Ugarov, San Jose, CA (US)

(73) Assignee: Thermo Finnigan LLC, San Jose, CA (US)

( * ) Notice: Subject to any disclaimer, the term of this patent is extended or adjusted under 35 U.S.C. 154(b) by 0 days.

(21) Appl. No.: 14/852,294

(22) Filed: Sep. 11, 2015

(51) Int. Cl.
  *H01J 49/04* (2006.01)
  *H01J 49/00* (2006.01)
  *H01J 49/42* (2006.01)

(52) U.S. Cl.
  CPC .......... *H01J 49/04* (2013.01); *H01J 49/0031* (2013.01); *H01J 49/421* (2013.01)

(58) Field of Classification Search
  USPC .................................. 250/283, 286, 281, 282
  See application file for complete search history.

(56) References Cited

U.S. PATENT DOCUMENTS

| | | | |
|---|---|---|---|
| 5,455,417 A | 10/1995 | Sacristan | |
| 5,847,386 A | 12/1998 | Thomson et al. | |
| 5,936,242 A | 8/1999 | De La Mora et al. | |
| 7,626,161 B2 | 12/2009 | Labowsky et al. | |
| 8,581,177 B2 * | 11/2013 | Kovtoun | H01J 49/004 250/281 |
| 8,766,176 B2 | 7/2014 | Park et al. | |
| 2003/0146377 A1 | 8/2003 | Miller et al. | |
| 2005/0029449 A1 | 2/2005 | Miller et al. | |
| 2007/0272852 A1 | 11/2007 | Miller et al. | |
| 2011/0183431 A1 | 7/2011 | Covey et al. | |
| 2012/0256083 A1 | 10/2012 | Kovtoun | |
| 2012/0325024 A1 | 12/2012 | Vidal-de-Miguel et al. | |
| 2014/0326870 A1 | 11/2014 | Makarov | |

(Continued)

FOREIGN PATENT DOCUMENTS

| | | |
|---|---|---|
| WO | 2004/012231 A2 | 2/2004 |
| WO | 2005/065307 A2 | 7/2005 |
| WO | 2006/130474 A2 | 12/2006 |

OTHER PUBLICATIONS

Rus, et al., "IMS—MS studies based on coupling a differential mobility analyzer (DMA) to commercial API—MS systems", Int. J.Mass.Spectrom., 2010, vol. 298 (1-3), pp. 30-40.

(Continued)

*Primary Examiner* — Kiet T Nguyen
(74) *Attorney, Agent, or Firm* — David A. Schell (57) ABSTRACT

A system for analyzing a sample includes a source configured to generate ions from constituent components of the sample; a mobility separation device, a plurality of ion channels, and a mass analyzer configured to determine the mass-to-charge ratio of the ions. The mobility device is configured to separate ions received from the source based on the mobility in a gas. The mobility separation device provides a gas flow in a first direction and an electric field gradient along a second direction such that ions move in the first direction and drift according to their mobility in the second direction and are sorted based on their respective mobility. The ion channels are arranged adjacent to the mobility separation device such that ions from the mobility separation device are directed to different channels according to their respective mobility.

30 Claims, 7 Drawing Sheets

(56) References Cited

U.S. PATENT DOCUMENTS

2014/0346339 A1 11/2014 Wu et al.
2015/0287585 A1* 10/2015 Kovtoun ............ H01J 49/4295
250/283

OTHER PUBLICATIONS

Loboda et al., "Novel Linac II electrode geometry for creating an axialfield in a multipole ion guide", European Journal of Mass Spectrometry, IM Publications 2000, vol. 6 (6), pp. 531-536.

* cited by examiner

SYSTEMS AND METHODS FOR ION SEPARATION

FIELD

The present disclosure generally relates to the field of mass spectrometry including systems and methods for ion separation.

INTRODUCTION

Filtering type mass spectrometry devices, such as quadrupole mass spectrometers, suffer from reduced efficiency (duty cycle) because they transmit ions of a single m/z ratio at a time while the rest are wasted. When performing an analysis of a complex sample, multiple analytes (N) can be targeted simultaneously by switching between ions and the duty cycle is limited to 1/N. While improvements can be made by only targeting transitions that correspond to ions eluting at a given moment, scheduling such experiments can be difficult when multiple ions elute at the same time or when retention times are unpredictable. Accumulating a broad range of ions in a trap and selectively ejecting them based on m/z to a quadrupole has the potential to avoid losing or missing ions while the quadrupole is analyzing only one m/z target at a time. However, mass resolving ion traps are limited to between about $10^7$ to about $10^9$ ions per second, which is significantly below the brightness of existing ion sources, which can generate about $10^{10}$ ions per second or more. As such, the potential gains would be negated by the inability to handle the entire load as compared to a normal flow-through regime with the quadrupole cycling between m/z ratios.

From the foregoing it will be appreciated that a need exists for improved systems and methods for separating ions before sending them to a filtering type mass spectrometry device.

SUMMARY

In a first aspect, a system for analyzing a sample can include a source configured to generate ions from constituent components of the sample; a mobility separator configured to separate ions received from the source based on the mobility in a gas; a plurality of ion channels arranged adjacent to the mobility separator such that ions from the mobility separator are directed to different channels according to their respective mobility; and a mass analyzer configured to determine the mass-to-charge ratio of the ions. The mobility separator can provide a gas flow in a first direction and an electric field gradient along a second direction such that ions move in the first direction and drift according to their mobility in the second direction such that the ions are sorted based on their respective mobility.

In various embodiments of the first aspect, the angle between the first direction and the second direction can be between about 45° and about 135°. In particular embodiments, the angle between the first direction and the second direction can be between about 70° and about 110°. In particular embodiments, the first direction and the second direction can be orthogonal.

In various embodiments of the first aspect, the ion channels can be selected from the group consisting of RF ion guides, ion traps, DC ion lenses, and a combination thereof.

In various embodiments of the first aspect, the system can further include a transfer guide configured to transport ions from the plurality of ion channel to the mass analyzer.

In various embodiments of the first aspect, individual ion channels can be defined by a plurality of rods. In particular embodiments, individual ion channels can have one or more drag vanes. In particular embodiments, the plurality of ion channels can include a plurality of guide rod pairs. The individual guide rods can extend along an ion channel length, guides rods of a guide rod pair can be separated in a first separation direction orthogonal to the ion channel length, and the pairs of guide rods separated in a second separation direction orthogonal to the ion channel length and the first separation direction. Adjacent ion channel can share a guide rod pair located between the adjacent ion channels. The plurality of drag vane pairs can be arranged such that individual drag vane pairs are positioned between adjacent guide rod pairs along the second separation direction such that individual ion channels have unique drag vane pairs.

In various embodiments of the first aspect, the plurality of ion channels can include between about 3 ion channels and about 50 ion channels. In particular embodiments, the plurality of ion channels can include between about 5 ion channels and about 20 ion channels. In particular embodiments, the plurality of ion channels can include between about 7 ion channels and about 15 ion channels.

In various embodiments of the first aspect, the electric field gradient in the mobility separator can be a substantially uniform electric field gradient. In various embodiments of the first aspect, the electric field gradient can be a non-uniform electric field gradient. In various embodiments of the first aspect, the electric field gradient can be generated by a series of discrete electrodes, one or more continuous resistive elements, or a combination thereof.

In various embodiments of the first aspect, a gas pressure within the mobility separator can be between about 1 Torr to about 20 Torr. In particular embodiments, the gas pressure within the mobility separator can be between about 3 Torr to about 6 Torr. In various embodiments of the first aspect, a gas flow within the mobility separator can be between about 15 slm and about 30 slm. In various embodiments of the first aspect, a gas velocity within the mobility separator can be between about 100 m/s and about 300 m/s. In particular embodiments, the gas velocity within the mobility separator can be between about 150 m/s and about 200 m/s.

In various embodiments of the first aspect, the system can further includes a lens array positioned between the mobility separator and the plurality of ion channels, the lens array configured to guide ions into respective ion channels.

In a second aspect, an ion mobility device for separating ions based on their ion mobility can include a mobility cell having a gas inlet and a gas outlet opposite the inlet along a first direction such that a gas flow introduced at the gas inlet would flow in a first direction to the gas outlet. The ion mobility cell can further have an ion entrance and a plurality of ion exit orifices opposite the ion entrance along a second direction and offset from the ion entrance and spaced apart from one another along the first direction. The ion mobility device can further include a plurality of electrodes configured to generate an electric field gradient in the second direction such that ions entering the mobility cell flow in the first direction with the gas and drift according to their mobility in the gas in the second direction. The ion mobility device can further include a plurality of ion channels arranged parallel to one another and arranged adjacent to the mobility cell at the plurality of ion exit orifices. The ion channels can be configured to receive ions from the mobility cell such that ions entering an individual ion channel have a range of ion mobilities that is different from a range of ion mobilities for ions entering an adjacent ion channel.

In various embodiments of the second aspect, a gas pressure within the mobility cell can be between about 1 Torr to about 20 Torr. In particular embodiments, the gas pressure within the mobility cell can be between about 3 Torr to about 6 Torr.

In various embodiments of the second aspect, a gas flow within the mobility cell can be between about 15 slm and about 30 slm. In various embodiments of the second aspect, a gas velocity within the mobility cell can be between about 100 m/s and about 300 m/s. In particular embodiments, a gas velocity within the mobility cell can be between about 150 m/s and about 200 m/s.

In various embodiments of the second aspect, the angle between the first direction and the second direction can be between about 45° and about 135°. In particular embodiments, the angle between the first direction and the second direction can be between about 70° and about 110°. In particular embodiments, the first direction and the second direction can be orthogonal.

In various embodiments of the second aspect, the ion channels can be selected from the group consisting of RF ion traps, ion guides, DC ion lenses, and combination thereof. In various embodiments of the second aspect, individual ion channels can be defined by a plurality of rods. In various embodiments of the second aspect, individual ion channels can have one or more drag vanes. In particular embodiments, the plurality of ion channels can include a plurality of guide rod pairs and a plurality of drag vane pairs. The individual guide rods can extend along an ion channel length with the guides rods of a guide rod pair separated in a first separation direction orthogonal to the ion channel length and the pairs of guide rods separated in a second separation direction orthogonal to the ion channel length and the first separation direction. Adjacent ion channels can share a guide rod pair located between the adjacent ion channels. The plurality of drag vane pairs can be arranged such that individual drag vane pairs are positioned between adjacent guide rod pairs along the second separation direction such that individual ion channels have unique drag vane pairs.

In various embodiments of the second aspect, the plurality of ion channels includes between about 3 ion channels and about 50 ion channels.

In particular embodiments, the plurality of ion channels can include between about 5 ion channels and about 20 ion channels. In particular embodiments, the plurality of ion channels can include between about 7 ion channels and about 15 ion channels.

In various embodiments of the second aspect, the electric field gradient can be generated by a series of discrete electrodes, one or more continuous resistive elements, or a combination thereof.

In various embodiments of the second aspect, the ion mobility device can further include a lens array positioned between the ion exit orifices and the plurality of ion channels. The lens array can be configured to guide ions into respective ion channels.

In a third aspect, a method for identifying components of a sample can include providing a sample to an ion source and generating a plurality of ions from constituent components of the sample; directing the ions into a mobility separator having a gas flow in a first direction and an electric field gradient along a second direction such that the ions move in the first direction and drift according to their mobility in the second direction; and separating the ions into a plurality of ion channels such that ions entering an individual ion channel have a range of ion mobilities that is different from a range of ion mobilities for ions entering an adjacent ion channel. The method can further include directing ions from individual ion channels into a mass analyzer; and using the mass analyzer to determine the mass-to-charge ratio of the ions.

In various embodiments of the third aspect, a gas pressure within the mobility separator can be between about 1 Torr to about 20 Torr. In particular embodiments, the gas pressure within the mobility separator can be between about 3 Torr to about 6 Torr. In various embodiments of the third aspect, a gas flow within the mobility separator can be between about 15 slm and about 30 slm. In various embodiments of the third aspect, a gas velocity within the mobility separator can be between about 100 m/s and about 300 m/s. In particular embodiments, the gas velocity within the mobility separator can be between about 150 m/s and about 200 m/s.

In various embodiments of the third aspect, the angle between the first direction and the second direction can be between about 45° and about 135°. In particular embodiments, the angle between the first direction and the second direction can be between about 70° and about 110°. In particular embodiments, the first direction and the second direction can be orthogonal.

In various embodiments of the third aspect, the ion channels can be selected from the group consisting of ion traps, ion guides, and quadrupolar mass filters. In various embodiments of the third aspect, individual ion channel can be defined by a plurality of rods. In particular embodiments, individual ion channels can have one or more drag vanes.

In particular embodiments, the plurality of ion channels can include a plurality of guide rod pairs and a plurality of drag vane pairs. The plurality of guide rod pairs can include individual guide rods extending along an ion channel length. The guide rods of a guide rod pair can be separated in a first separation direction orthogonal to the ion channel length, and the pairs of guide rods can be separated in a second separation direction orthogonal to the ion channel length and the first separation direction, such that adjacent ion channels share a guide rod pair located between the adjacent ion channels. The plurality of drag vane pairs can be arranged such that individual drag vane pairs are positioned between adjacent guide rod pairs along the second separation direction such that individual ion channels have unique drag vane pairs.

In various embodiments of the third aspect, the plurality of ion channels can include between about 3 ion channels and about 50 ion channels. In particular embodiments, the plurality of ion channels can include between about 5 ion channels and about 20 ion channels. In particular embodiments, the plurality of ion channels can include between about 7 ion channels and about 15 ion channels.

In various embodiments of the third aspect, the electric field gradient can be generated by a series of discrete electrodes, one or more continuous resistive elements, or a combination thereof.

DRAWINGS

For a more complete understanding of the principles disclosed herein, and the advantages thereof, reference is now made to the following descriptions taken in conjunction with the accompanying drawings, in which.

It is to be understood that the figures are not necessarily drawn to scale, nor are the objects in the figures necessarily drawn to scale in relationship to one another. The figures are depictions that are intended to bring clarity and understanding to various embodiments of apparatuses, systems, and methods disclosed herein. Wherever possible, the same reference numbers will be used throughout the drawings to refer to the same or like parts. Moreover, it should be appreciated that the drawings are not intended to limit the scope of the present teachings in any way.

DESCRIPTION OF VARIOUS EMBODIMENTS

Embodiments of systems and methods for ion separation are described herein.

The section headings used herein are for organizational purposes only and are not to be construed as limiting the described subject matter in any way.

In this detailed description of the various embodiments, for purposes of explanation, numerous specific details are set forth to provide a thorough understanding of the embodiments disclosed. One skilled in the art will appreciate, however, that these various embodiments may be practiced with or without these specific details. In other instances, structures and devices are shown in block diagram form. Furthermore, one skilled in the art can readily appreciate that the specific sequences in which methods are presented and performed are illustrative and it is contemplated that the sequences can be varied and still remain within the spirit and scope of the various embodiments disclosed herein.

All literature and similar materials cited in this application, including but not limited to, patents, patent applications, articles, books, treatises, and internet web pages are expressly incorporated by reference in their entirety for any purpose. Unless described otherwise, all technical and scientific terms used herein have a meaning as is commonly understood by one of ordinary skill in the art to which the various embodiments described herein belongs.

It will be appreciated that there is an implied "about" prior to the temperatures, concentrations, times, pressures, flow rates, cross-sectional areas, etc. discussed in the present teachings, such that slight and insubstantial deviations are within the scope of the present teachings. In this application, the use of the singular includes the plural unless specifically stated otherwise. Also, the use of "comprise", "comprises", "comprising", "contain", "contains", "containing", "include", "includes", and "including" are not intended to be limiting. It is to be understood that both the foregoing general description and the following detailed description are exemplary and explanatory only and are not restrictive of the present teachings.

As used herein, "a" or "an" also may refer to "at least one" or "one or more." Also, the use of "or" is inclusive, such that the phrase "A or B" is true when "A" is true, "B" is true, or both "A" and "B" are true. Further, unless otherwise required by context, singular terms shall include pluralities and plural terms shall include the singular.

A "system" sets forth a set of components, real or abstract, comprising a whole where each component interacts with or is related to at least one other component within the whole.

Mass Spectrometry Platforms

Figure 1:
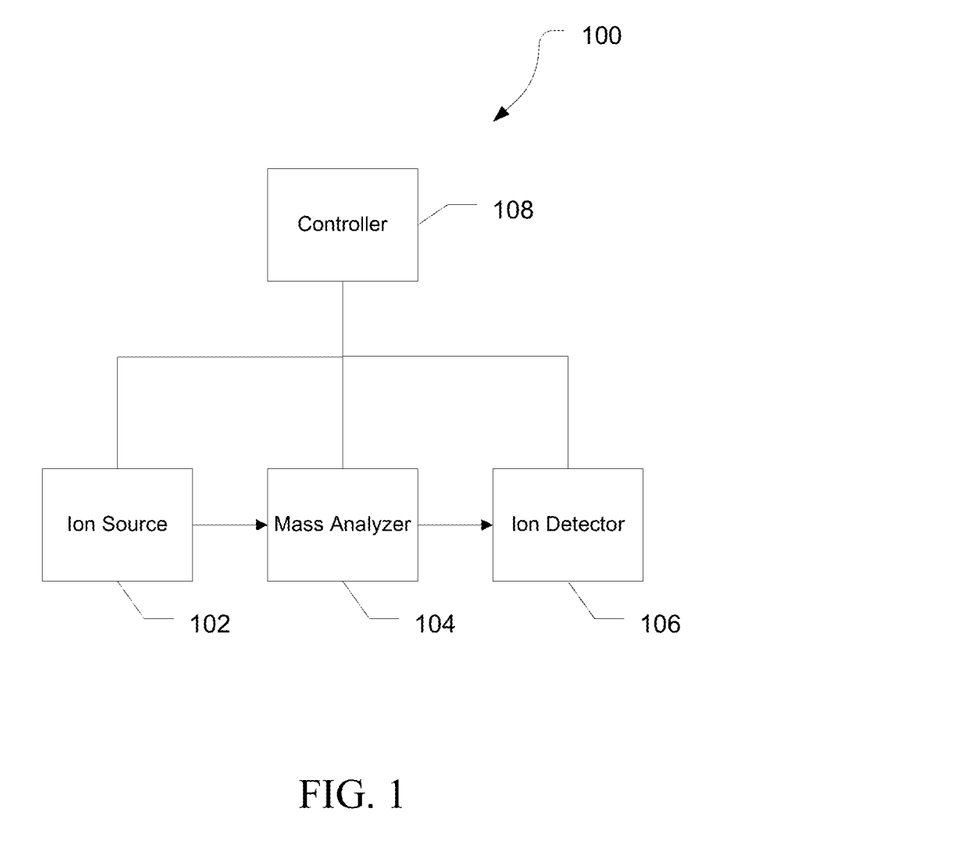
FIG. 1 is a block diagram of an exemplary mass spectrometry system, in accordance with various embodiments.

Various embodiments of mass spectrometry platform 100 can include components as displayed in the block diagram of FIG. 1. In various embodiments, elements of FIG. 1 can be incorporated into mass spectrometry platform 100. According to various embodiments, mass spectrometer 100 can include an ion source 102, a mass analyzer 104, an ion detector 106, and a controller 108.

In various embodiments, the ion source 102 generates a plurality of ions from a sample. The ion source can include, but is not limited to, a matrix assisted laser desorption/ionization (MALDI) source, electrospray ionization (ESI) source, atmospheric pressure chemical ionization (APCI) source, atmospheric pressure photoionization source (APPI), inductively coupled plasma (ICP) source, electron ionization source, chemical ionization source, photoionization source, glow discharge ionization source, thermospray ionization source, and the like.

In various embodiments, the mass analyzer 104 can separate ions based on a mass-to-charge ratio of the ions. For example, the mass analyzer 104 can include a quadrupole mass filter analyzer, a quadrupole ion trap analyzer, a time-of-flight (TOF) analyzer, an electrostatic trap (e.g., Orbitrap) mass analyzer, Fourier transform ion cyclotron resonance (FT-ICR) mass analyzer, and the like. In various embodiments, the mass analyzer 104 can also be configured to fragment the ions using collision induced dissociation (CID) electron transfer dissociation (ETD), electron capture dissociation (ECD), photo induced dissociation (PID), surface induced dissociation (SID), and the like, and further separate the fragmented ions based on the mass-to-charge ratio.

In various embodiments, the ion detector 106 can detect ions. For example, the ion detector 106 can include an electron multiplier, a Faraday cup, and the like. Ions leaving the mass analyzer can be detected by the ion detector. In various embodiments, the ion detector can be quantitative, such that an accurate count of the ions can be determined.

In various embodiments, the controller 108 can communicate with the ion source 102, the mass analyzer 104, and the ion detector 106. For example, the controller 108 can configure the ion source or enable/disable the ion source. Additionally, the controller 108 can configure the mass analyzer 104 to select a particular mass range to detect. Further, the controller 108 can adjust the sensitivity of the ion detector 106, such as by adjusting the gain. Additionally, the controller 108 can adjust the polarity of the ion detector 106 based on the polarity of the ions being detected. For example, the ion detector 106 can be configured to detect positive ions or be configured to detected negative ions.

Low Pressure Ion Mobility Separation

Figure 2:
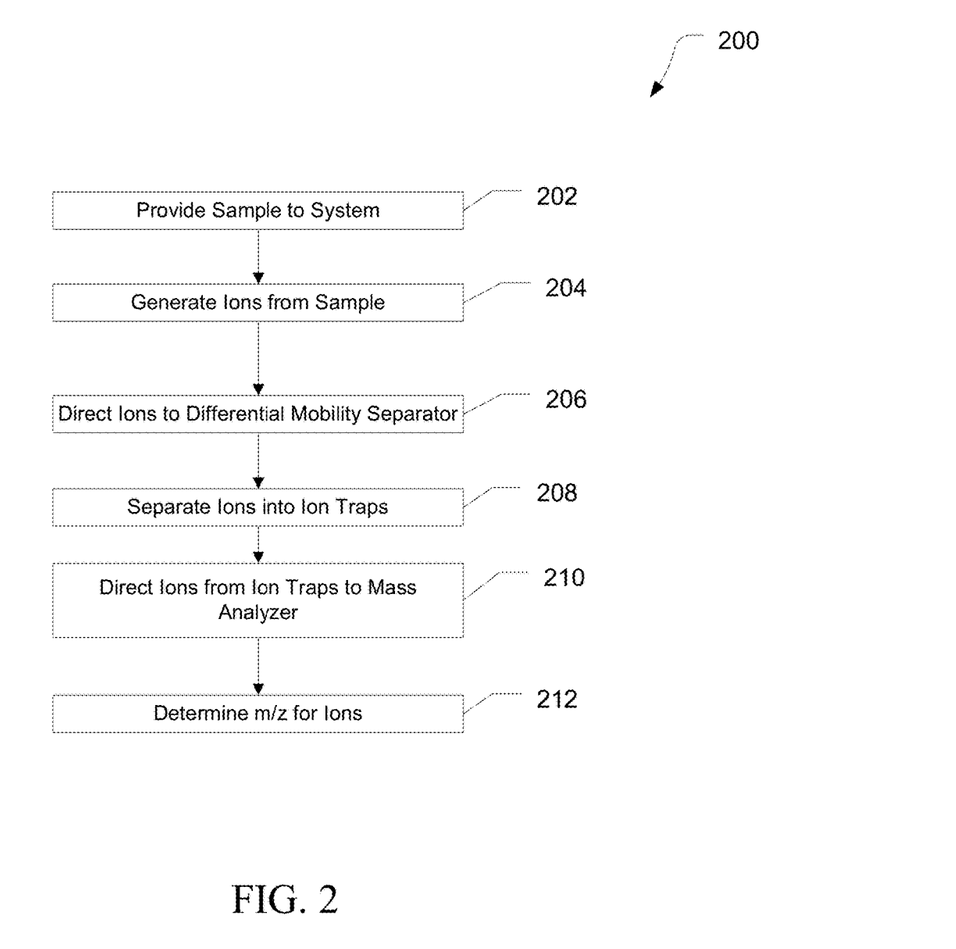
FIG. 2 is a flow diagram of an exemplary method for separating ions, in accordance with various embodiments.

FIG. 2 is a flow diagram illustrating an exemplary method 200 of separating ions according to their mobility in order to increase the efficiency of a mass spectrometry platform, such as mass spectrometry platform 100 in FIG. 1.

At 202, a sample can be provided to a system. In various embodiments, the sample can be effluent from a liquid chromatography column, effluent from a gas chromatography column, a directly injected sample (liquid or gas), or a sample embedded in a solid matrix.

At 204, they system can generate ions from the sample. The sample can enter into an ion source to generate ions. The ion source can utilize various energy sources, such as electrical, light, plasma, chemical, electrons, heat, or the like to ionize the sample or components of the sample.

At 206, the ions can move from the source into a mobility separator. In various embodiments, the mobility separator can include a flow of gas in a first direction and an electrical field in a second direction. In various embodiments, the ions can move with a substantially similar velocity in the first direction due to the flow of the gas. However, the velocity in the second direction can be affected by collisions with the gas ions, and thus larger ions (with a greater collisional cross section) will move more slowly in the second direction, resulting in a separation of the ions along the first direction being a function of transit time in the second direction. That is, larger ions that move more slowly in the second direction will move further in the first direction in the time it takes for them to traverse the mobility separator in the second direction, while smaller ions will move faster across the mobility separator, and thus the distance traveled will be smaller. In this way, ions entering an ion channel can have a different range on ion mobilities to ions entering an adjacent ion channel.

At 208, the ions can be separated and delivered into a plurality of ion channels arranged along the first direction of the mobility separator. Smaller ions can enter an ion channel located a smaller distance along the first direction relative to the ion entrance, while larger ions can enter an ion channel located a larger distance along the first direction relative to the ion entrance. As ions enter the mobility separator, the can be accumulated in the ion channels based on their ion mobility.

In various embodiments, the ion channels can include ion traps, RF ion guides, DC ion lenses, or a combination thereof. In particular embodiments, the ion channels can include ion traps each defined by a plurality of rods. Additionally, each ion trap can include one or more drag vanes. In certain embodiments, adjacent ion traps in the array of ion traps can share a pair of rods.

At 210, ions can be ejected from one of the ion channels/traps and sent to a mass analyzer. In alternate embodiments, the ions may undergo other processes prior to reaching the mass analyzer, such as separations based on mass-to-charge ratio, fragmentations, or the like. In various embodiments, the ions of other mobility can continue to be accumulated in their respective traps. Additionally, the ions can be sequentially ejected from a plurality of the ion channels/traps, so that the ions can be analyzed.

At 212, the mass analyzer can determine the mass-to-charge ratio of the ions, or the fragments of the ions if the ions undergo fragmentation prior to the mass analyzer.

Figure 3:
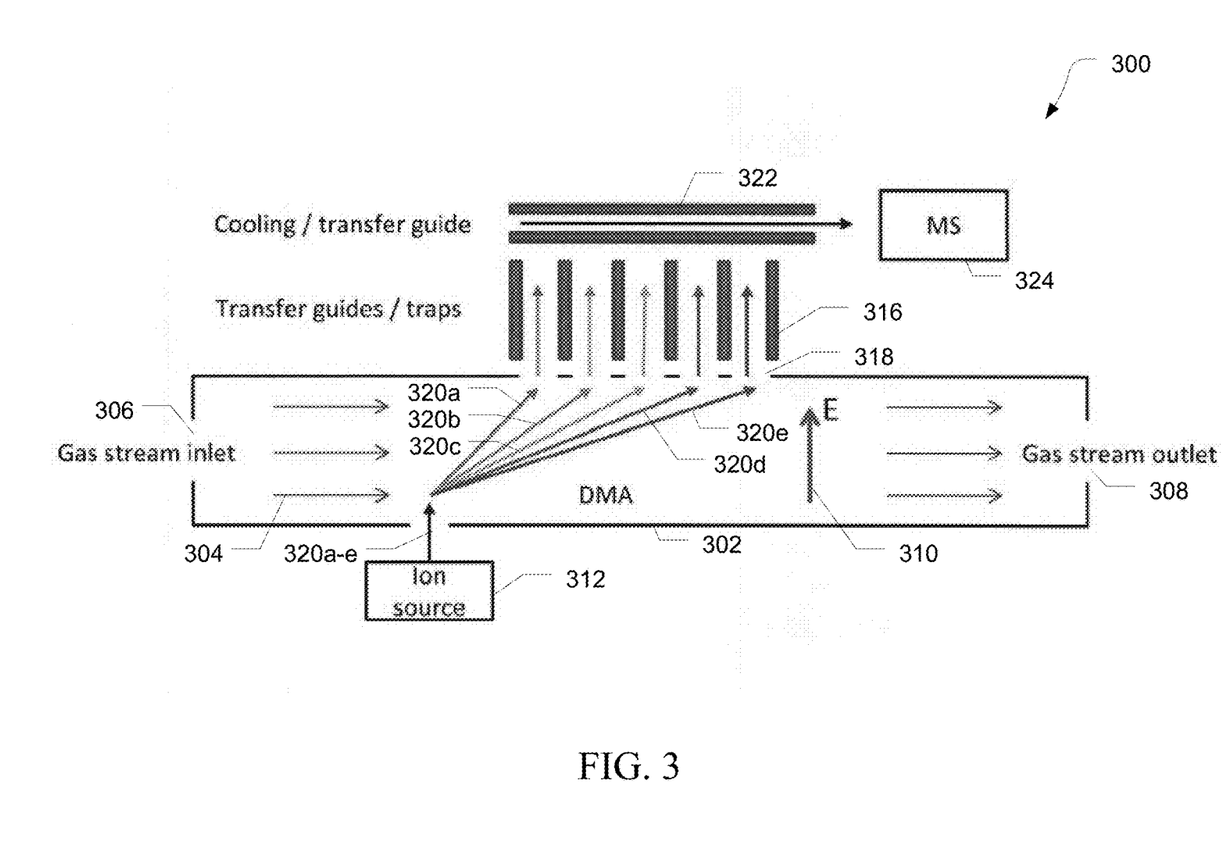
FIG. 3 is a block diagram illustrating an exemplary ion mobility separator, in accordance with various embodiments.

FIG. 3 is a block diagram illustrating a mobility separator 300. The mobility separator 300 can include a mobility cell 302 consisting of a region, such as a substantially rectangular region, with a gas flow 304 moving in a first direction from a gas inlet 306 at one end to a gas outlet 308 at the opposite end. Additionally, an electrical field gradient 310 can be applied in a second direction. In various embodiments, the first direction and the second direction can form an angle of between about 45° and 135°, such as between about 70° and about 110°. In particular embodiments, the first direction and the second direction can be orthogonal (at right angles, perpendicular) to one another.

In various embodiments, a gas pressure within the mobility cell 302 can be between about 1 Torr and about 20 Torr, such as between about 3 Torr and about 6 Torr. In various embodiments, the gas flow can be between about 15 slm and about 30 slm. In various embodiments, the gas velocity within the mobility analyzer cell 302 can be between about 100 m/s and about 300 m/s, such as between about 150 m/s and about 200 m/s.

An ion source 312 can be located proximal to an ion entrance 314 and an array of ion channels 316 can be located proximal to an array of ion exit orifices 318. The ion exit orifices 318 can be located opposite the ion entrance 314 in the second direction, and can be offset from the ion entrance 314 and spaced apart from one another in the first direction. Ions 320a through 320e entering the mobility cell 302 from the ion source 312 can be separated into the ion exit orifices 318 and directed into the array of ion channels 316 in accordance with their ion mobility within the mobility cell 302. In various embodiments, the ions 320a through 320e can flow at a substantially the same velocity along the first direction and may move in the second direction according to their collisional cross section. Thus, ions 320e with a larger collisional cross section can move more slowly in the second direction due to a larger number of collisions with the molecules in the gas flow relative to ions with a smaller collisional cross section 320a. Due to the slower movement in the second direction, ions 320e can move further along the first direction during their transit across the mobility cell 302. In this way, ions with successively larger collisional cross section can be sorted into the array of ion channels 316, such that ions in an ion channel have a different range of ion mobilities from ions in an adjacent ion channel.

In various embodiments, a lens array (not shown) can be positioned between the ion exit orifices 318 and the ion channels 316. The lens array can be configured to guide ions into the respective channel, such as by focusing the ions towards the centerline of the channel.

In various embodiments, the plurality of ion channels 316 can include between about 3 ion channels and about 50 ion channels, such as between about 5 ion channels and about 20 ion channels, even between about 7 ion channels and about 15 ions traps.

A cooling/transfer guide 322 can be located adjacent to the plurality of ion channels 316. Ions can be ejected from one of the ion channels 316 into the cooling/transfer guide 322. From the cooling/transfer guide 322, the ions can be directed to a mass analyzer 324. In various embodiments, the ions may be directed to other processes, such as a fragmentation cell (not shown), prior to the mass analyzer.

In various embodiments, the mobility separator system 300 can separate ions spatially to allow only one or a few types of ions to be directed to the mass analyzer at a time while capturing multiple groups of ions that can be stored in traps and subsequently injected into the mass analyzer. The ejections from the ion channels 316 can allow the mass analyzer to perform mass analysis of an ion packet while other ions continue to be accumulated and stored in the ion traps 316. The potential gain provided by the mobility separator can be equal to the number of separate channels.

Figure 4:
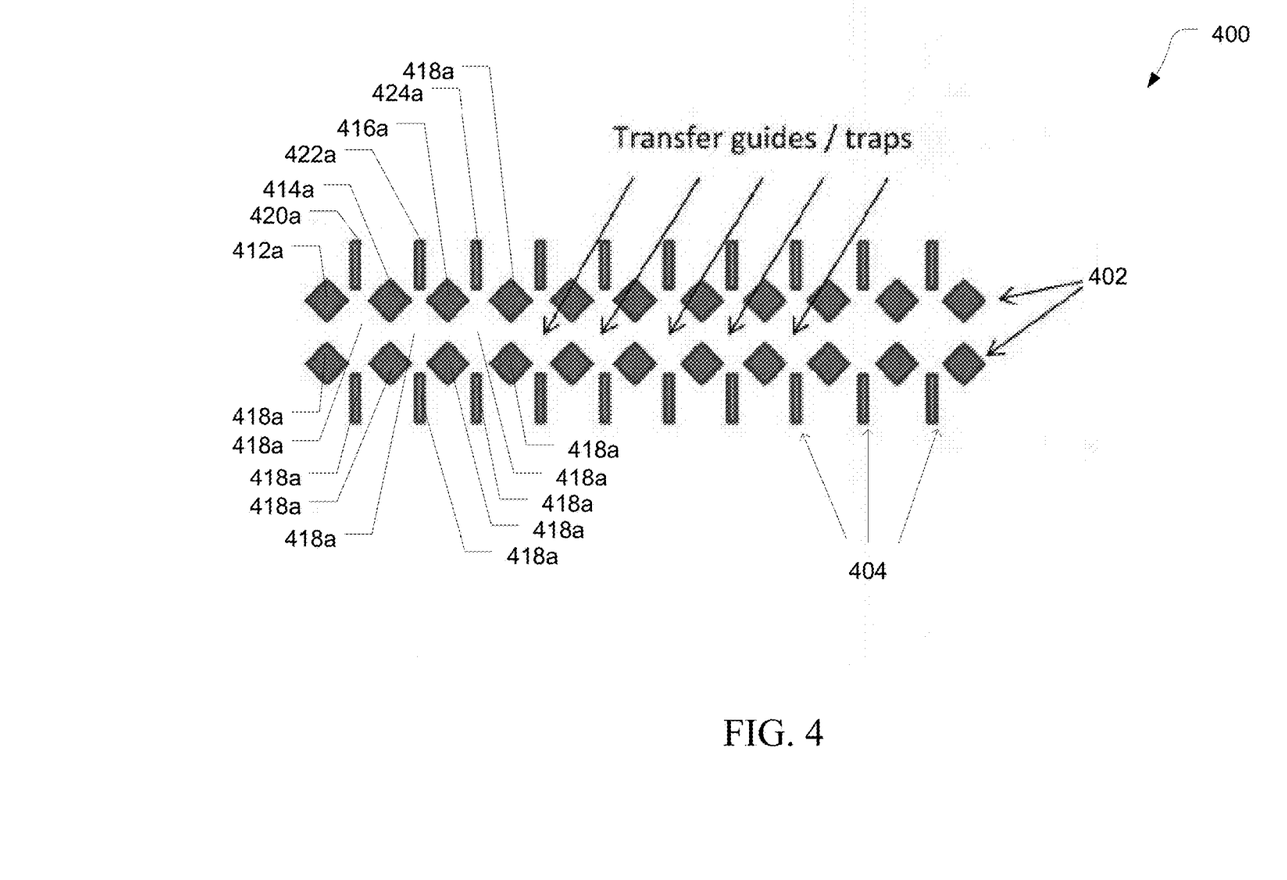
FIG. 4 is a block diagram illustrating an exemplary array of ion channels, in accordance with various embodiments.

FIG. 4 is a block diagram illustrating an exemplary array of ion channels 400, such as the array of ion channels 316 in FIG. 3. In various embodiments, the array of ion channels 400 can include an array of quadrupole rod pairs 402 and an array of drag vane pairs 404. Each ion channel, such as ion channels 406, 408, and 410, can be defined by 4 quadrupole rods (2 pairs). For example, ion channel 406 is defined by quadrupole rods 412a, 412b, 414a, and 414b, ion channel 408 is defined by quadrupole rods 414a, 414b, 416a, and 416b, and ion channel 410 is defined by quadrupole rods 416a, 416b, 418a, and 418b. Additionally, adjacent ion channels can share a quadrupole rod pair between them, for example, ion channels 406 and 408 share quadrupole rods 414a and 414b, and ion channels 408 and 410 share quadrupole rods 416a and 416b. The quadrupole rods can create a quadrupolar field in each ion channel to confine ions within the channel.

Additional stopping DC voltages can be applied to the optical element before and after the set of quadrupole rods to trap ions inside the channels which in this case operate as ion traps. When needed, these voltages can be lowered quickly to release ions from the channels.

Additionally, in order to ensure quick release ions only from specific channels, each ion channel can include a corresponding pair of drag vanes. For example, ion channel 406 can have include drag vanes 420a and 420b, ion channel 408 can have include drag vanes 422a and 422b, and ion channel 410 can have include drag vanes 424a and 424b. By placing a DC gradient along a pair of drag vanes, ions can be driven out of the channel, such as into the cooling/transfer guide 322 of FIG. 3. Additional, as each ion channel has a unique pair of drag vanes, ions can be driven from one ion channel without driving ions from an adjacent ion channel.

Figure 5A:
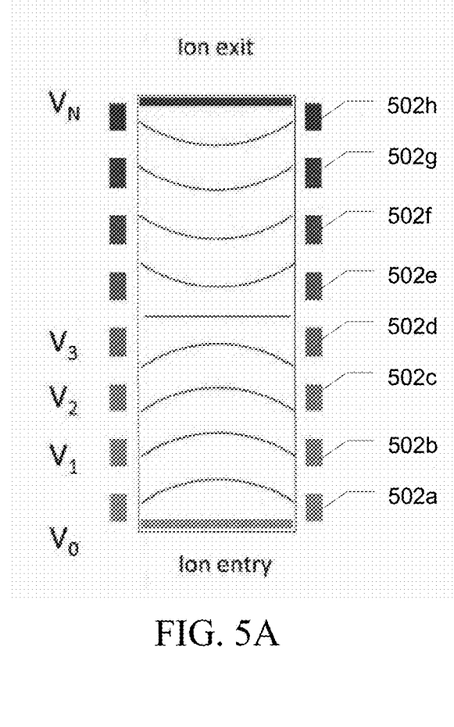
FIGS. 5A, 5B, and 5C are exemplary electrode arrangements for creating an electrical field gradient across an ion mobility separator, in accordance with various embodiments.
Figure 5B:
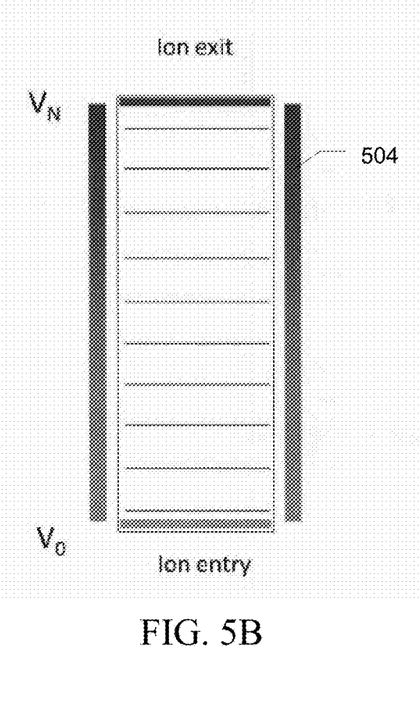
Figure 5C:
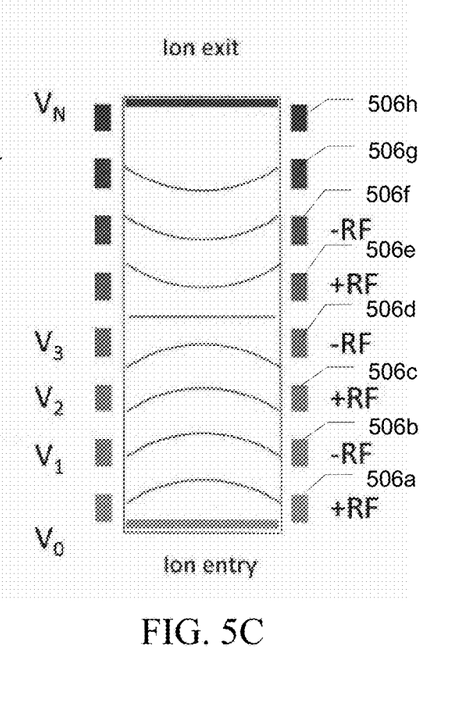

FIGS. 5A through 5C show electrode arrangements for establishing the electric field gradient along the second direction of the mobility cell, such as mobility cell 302 in FIG. 3. FIG. 5A illustrates the use of a set of discrete electrodes (502a through 502h) on the walls of the mobility analyzer cell. The discrete electrodes can have increasing DC potentials going from $V_0$ proximal to the ion entrance to $V_N$ proximal to the ion exit. Additionally, in various embodiments, the discrete electrodes can be configured to establish a non-uniform electric field gradient, such that the electric field gradient systematically varies. Such an electric field gradient can partially confine and focus ions towards the centerline to compensate for diffusion broadening.

FIG. 5B illustrates the use of a resistive layer 504 to generate a continuous potential distribution from $V_0$ proximal to the ion entrance to $V_N$ proximal to the ion exit. Resistive layer 504 can be used to establish a substantially uniform electric field gradient.

FIG. 5C illustrates a set of discrete electrodes (506a through 506h) on the walls of the mobility cell, with the discrete electrodes configured with alternating RF potentials to confine ions towards the center and increasing DC potentials going from $V_0$ proximal to the ion entrance to $V_N$ proximal to the ion exit.

While the present teachings are described in conjunction with various embodiments, it is not intended that the present teachings be limited to such embodiments. On the contrary, the present teachings encompass various alternatives, modifications, and equivalents, as will be appreciated by those of skill in the art.

Further, in describing various embodiments, the specification may have presented a method and/or process as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process should not be limited to the performance of their steps in the order written, and one skilled in the art can readily appreciate that the sequences may be varied and still remain within the spirit and scope of the various embodiments.

Simulation Results

Figure 6:
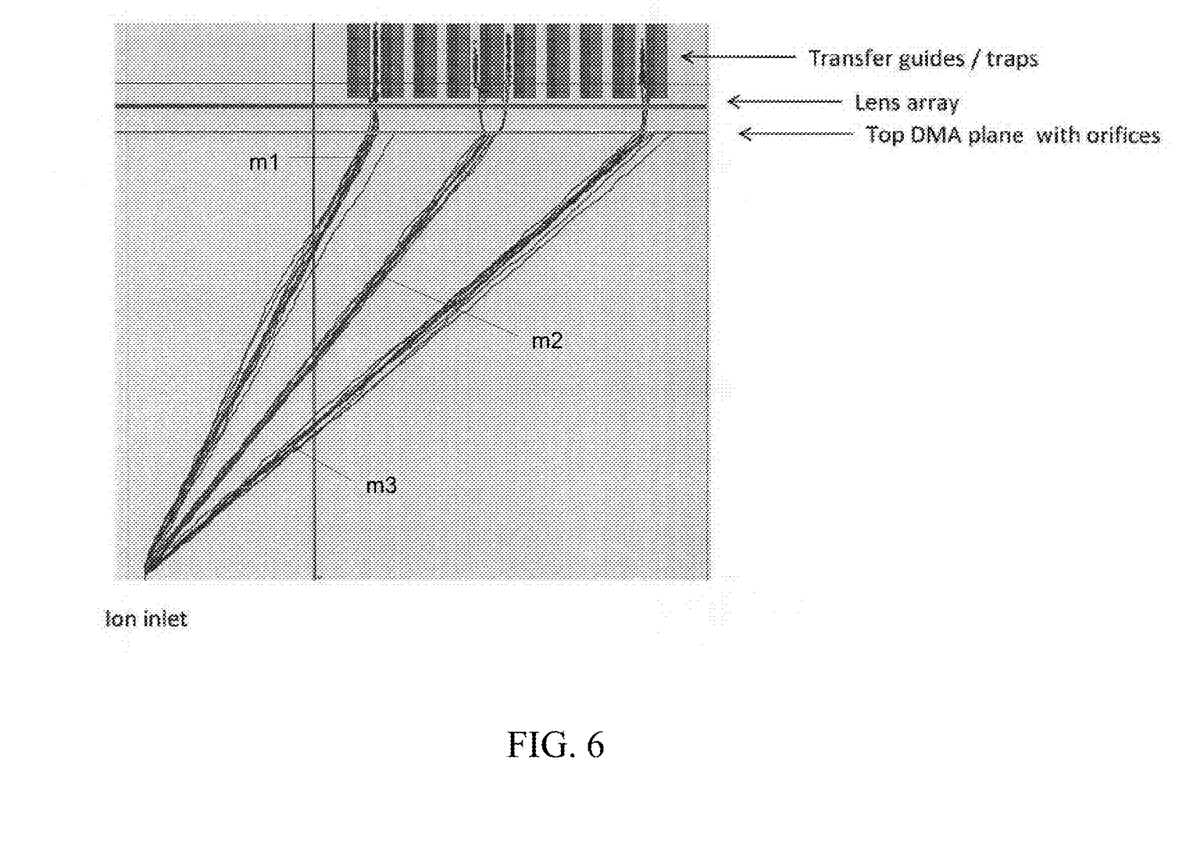
FIGS. 6 and 7 are illustrations of ion simulations within an exemplary ion mobility separator.

FIG. 6 shows results of a SIMION simulation of a 9-channel DMA ion mobility separator. Parameters are shown in Table 1. Separation of three different mass ions are simulated including m1 has a mass of 300 Da and a collisional cross section of 1 nm, m2 has a mass of 600 Da and a collisional cross section of 1.6 nm, and m3 has a mass of 1000 Da and a collisional cross section of 2.4 nm. The simulation shows the ions are separated into different ion channels, with the m1 ions entering the first ion channel, the m3 ions entering the last ion channel, and the m2 ions being split between the fourth and fifth ion channels.

Figure 7:
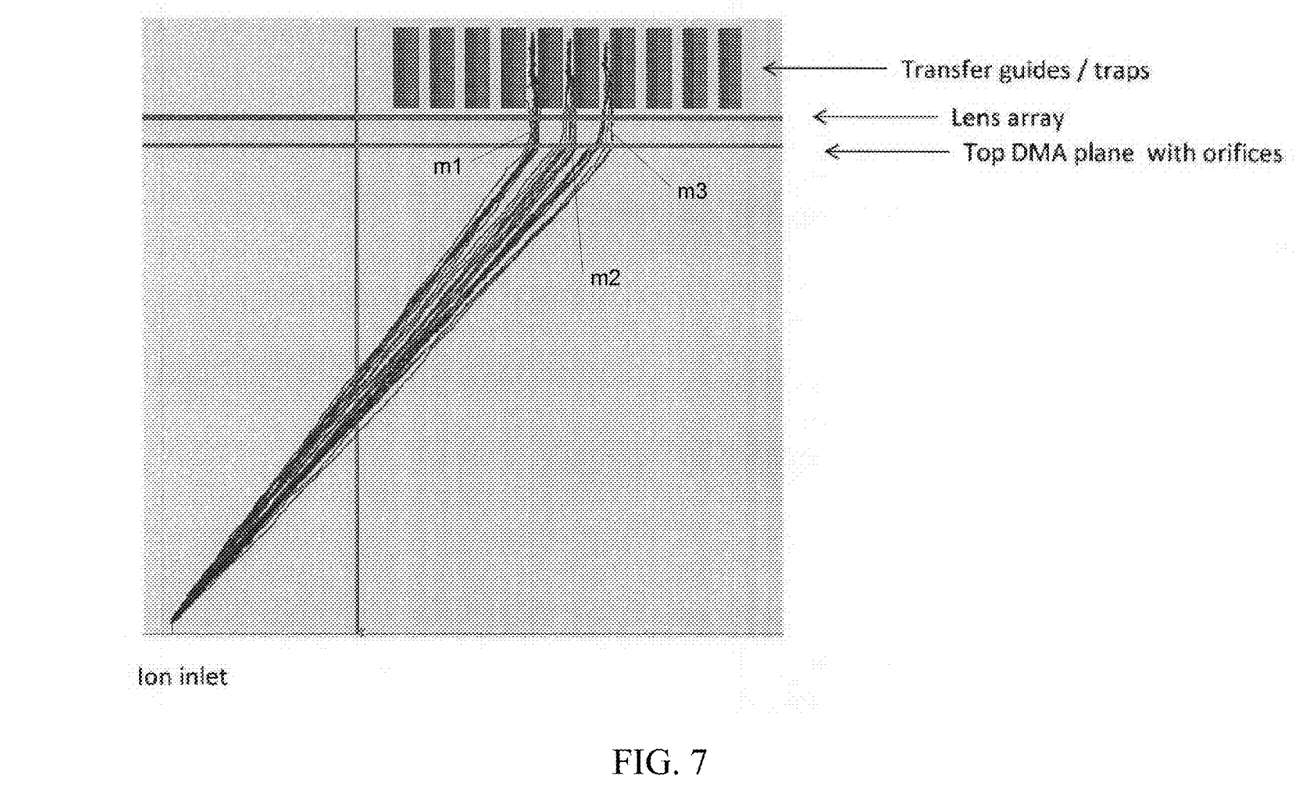

FIG. 7 shows results of a SIMION simulation of a 9-channel DMA ion mobility separator. Separation of three different mass ions are simulated including m1 has a mass of 300 Da and a collisional cross section of 1.6 nm, m2 has a mass of 350 Da and a collisional cross section of 1.6 nm, and m3 has a mass of 400 Da and a collisional cross section of 1.6 nm. The simulation shows the ions are separated into different ion channels, with the m1 ions entering the fourth ion channel, the m2 ions being entering the fifth ion channel, and the m3 ions entering the sixth ion channel.

TABLE 1

| Parameter | FIG. 6 | FIG. 7 |
| --- | --- | --- |
| Dimensions | 40 mm × 50 mm × 10 mm | 40 mm × 50 mm × 10 mm |
| Pressure | 3 Torr Nitrogen | 6 Torr Nitrogen |
| Gas Flow | 17 slm | 35 slm |
| Gas Velocity | 180 m/s | 180 m/s |
| Electric Field | 250 V | 400 V |
| Outlet Array Width | 30 mm | 30 mm |
| Separation Resolution | About 15 | About 20 |
| Separation Time | 300 μsec | 300 μsec |
| Reynolds Number | About 500 | About 1000 |

What is claimed is:

1. A system for analyzing a sample comprising:
   a source configured to generate ions from constituent components of the sample;
   a mobility separator configured to separate ions received from the source based on the mobility in a gas; the mobility separator providing a gas flow in a first direction and an electric field gradient along a second direction such that ions move in the first direction and drift according to their mobility in the second direction such that the ions are sorted based on their respective mobility;
   a plurality of ion channels arranged adjacent to the mobility separator such that ions from the mobility separator are directed to different channels according to their respective mobility; and
   a mass analyzer configured to determine the mass-to-charge ratio of the ions.

2. The system of claim 1, wherein an angle between the first direction and the second direction is between about 45° and about 135°.

3. The system of claim 2, wherein the first direction and the second direction are orthogonal.

4. The system of claim 1, wherein the ion channels are selected from the group consisting of RF ion guides, ion traps, DC ion lenses, and a combination thereof.

5. The system of claim 1 further comprising a transfer guide configured to transport ions from the plurality of ion channel to a mass analyzer.

6. The system of claim 1, wherein each ion channels is defined by a plurality of rods.

7. The system of claim 6, wherein each ion channels has one or more drag vanes.

8. The system of claim 7, wherein the plurality of ion channels comprise:
a plurality of guide rod pairs, individual guide rods extending along an ion channel length, guides rods of a guide rod pair separated in a first separation direction orthogonal to the ion channel length, and the pairs of guide rods separated in a second separation direction orthogonal to the ion channel length and the first separation direction, such that adjacent ion channel share a guide rod pair located between the adjacent ion channels; and
a plurality of drag vane pairs arranged such that individual drag vane pairs are positioned between adjacent guide rod pairs along the second separation direction such that individual ion channels have unique drag vane pairs.

9. The system of claim 1, wherein the plurality of ion channels includes between about 3 ion channels and about 50 ion channels.

10. The system of claim 9, wherein the plurality of ion channels includes between about 5 ion channels and about 20 ion channels.

11. The system of claim 10, wherein the plurality of ion channels includes between about 7 ion channels and about 15 ion channels.

12. The system of claim 1, wherein the electric field gradient is a substantially uniform electric field gradient.

13. The system of claim 1, wherein the electric field gradient is a non-uniform electric field gradient.

14. The system of claim 1, wherein a gas pressure within the mobility separator is between about 1 Torr to about 20 Torr.

15. The system of claim 14, wherein the gas pressure within the mobility separator is between about 3 Torr to about 6 Torr.

16. The system of claim 1, wherein a gas flow within the mobility separator is between about 15 slm and about 30 slm.

17. The system of claim 1, wherein a gas velocity within the mobility separator is between about 100 m/s and about 300 m/s.

18. The system of claim 17, wherein the gas velocity within the mobility separator is between about 150 m/s and about 200 m/s.

19. The system of claim 1 further comprising a lens array positioned between the mobility separator and the plurality of ion channels, the lens array configured to guide ions into respective ion channels.

20. An ion mobility device for separating ions based on their ion mobility, comprising:
a mobility cell having a gas inlet and a gas outlet opposite the inlet along a first direction such that a gas flow introduced at the gas inlet would flow in a first direction to the gas outlet, an ion entrance and a plurality of ion exit orifices opposite the ion entrance along a second direction and offset from the ion entrance and spaced apart from one another along the first direction,
a plurality of electrodes configured to generate an electric field gradient in the second direction such that ions entering the mobility cell flow in the first direction with the gas and drift according to their mobility in the gas in the second direction; and
a plurality of ion channels arranged parallel to one another and arranged adjacent to the mobility cell at the plurality of ion exit orifices, the ion channels configured to receive ions from the mobility cell such that ions entering an individual channel have a range of ion mobilities that is different from a range of ion mobilities for ions entering an adjacent ion channel.

21. The ion mobility device of claim 20, wherein the ion channels are selected from the group consisting of RF ion traps, ion guides, DC ion lenses, and combination thereof.

22. The ion mobility device of claim 20, wherein the electric field gradient is generated by a series of discrete electrodes, one or more continuous resistive elements, or a combination thereof.

23. The ion mobility device of claim 20 further comprising a lens array positioned between the ion exit orifices and the plurality of ion channels, the lens array configured to guide ions into respective ion channels.

24. A method for identifying components of a sample comprising:
providing a sample to an ion source and generating a plurality of ions from constituent components of the sample;
directing the ions into a mobility separator having a gas flow in a first direction and an electric field gradient along a second direction such that the ions move in the first direction and drift according to their mobility in the second direction;
separating the ions into a plurality of ion channels such that ions entering an individual ion channel have a range of ion mobilities that is different from a range of ion mobilities for ions entering an adjacent ion channel;
directing ions from individual ion channels into a mass analyzer; and
using the mass analyzer to determine the mass-to-charge ratio of the ions.

25. The method of claim 24, wherein a gas flow within the mobility separator is between about 15 slm and about 30 slm.

26. The method of claim 24, wherein a gas velocity within the mobility separator is between about 100 m/s and about 300 m/s.

27. The method of claim 24, wherein an angle between the first direction and the second direction is between about 45° and about 135°.

28. The method of claim 27, wherein the first direction and the second direction are orthogonal.

29. The method of claim 24, wherein the plurality of ion channels comprise:
a plurality of guide rod pairs, individual guide rods extending along an ion channel length, guides rods of a guide rod pair separated in a first separation direction orthogonal to the ion channel length, and the pairs of guide rods separated in a second separation direction orthogonal to the ion channel length and the first separation direction, such that adjacent ion channels share a guide rod pair located between the adjacent ion channels; and
a plurality of drag vane pairs arranged such that individual drag vane pairs are positioned between adjacent guide rod pairs along the second separation direction such that individual ion channels have unique drag vane pairs.

30. The method of claim 24, wherein the electric field gradient is generated by a series of discrete electrodes, one or more continuous resistive elements, or a combination thereof.

* * * * *